(12) United States Patent
Bowman et al.

(10) Patent No.: US 6,780,182 B2
(45) Date of Patent: Aug. 24, 2004

(54) CATHETER PLACEMENT DETECTION SYSTEM AND OPERATOR INTERFACE

(75) Inventors: Brett S. Bowman, Redwood City, CA (US); Vijay Dhaka, Redwood City, CA (US); Kenneth Kitlas, Freemont, CA (US); Douglas C. Harrington, Redwood City, CA (US)

(73) Assignee: Adiana, Inc., Redwood City, CA (US)

( * ) Notice: Subject to any disclaimer, the term of this patent is extended or adjusted under 35 U.S.C. 154(b) by 0 days.

(21) Appl. No.: 10/155,462

(22) Filed: May 23, 2002

(65) Prior Publication Data

US 2003/0220636 A1 Nov. 27, 2003

(51) Int. Cl.[7] .............................................. A61B 18/18
(52) U.S. Cl. ............................ 606/41; 606/31; 606/34; 606/28; 606/38; 606/42; 606/48; 607/101
(58) Field of Search ............................. 606/34, 41, 48, 606/28, 31, 38, 42; 607/101

(56) References Cited

U.S. PATENT DOCUMENTS

| | | | |
|---|---|---|---|
| 3,949,736 A | 4/1976 | Vrana et al. ............. | 128/2.1 Z |
| 4,245,643 A | 1/1981 | Benzing, III et al. ....... | 128/419 |
| 5,203,344 A | 4/1993 | Scheltinga et al. ......... | 128/734 |
| 5,341,807 A * | 8/1994 | Nardella ..................... | 600/381 |
| 5,469,857 A * | 11/1995 | Laurent et al. ............. | 600/523 |
| 5,673,704 A | 10/1997 | Marchlinski et al. ....... | 128/739 |
| 5,836,990 A | 11/1998 | Li .............................. | 607/28 |
| 5,954,715 A | 9/1999 | Harrington et al. .......... | 606/28 |
| 6,309,384 B1 | 10/2001 | Harrington et al. .......... | 606/28 |
| 6,391,024 B1 * | 5/2002 | Sun et al. .................... | 606/34 |
| 6,569,160 B1 * | 5/2003 | Goldin et al. ................ | 606/41 |

* cited by examiner

*Primary Examiner*—Roy D. Gibson
*Assistant Examiner*—Aaron Roane
(74) *Attorney, Agent, or Firm*—K. David Crockett, Esq.; Crockett & Crockett

(57) ABSTRACT

A system for facilitating the placement of a catheter within the human body, in a lumen or vessel such as the fallopian tubes, and controlling the catheter after placement. The system coordinates the operation of treatment electrodes on the catheter with informative displays and prompts to an operator, based on information derived from electrical parameters of position detection electrodes on the catheter.

31 Claims, 9 Drawing Sheets

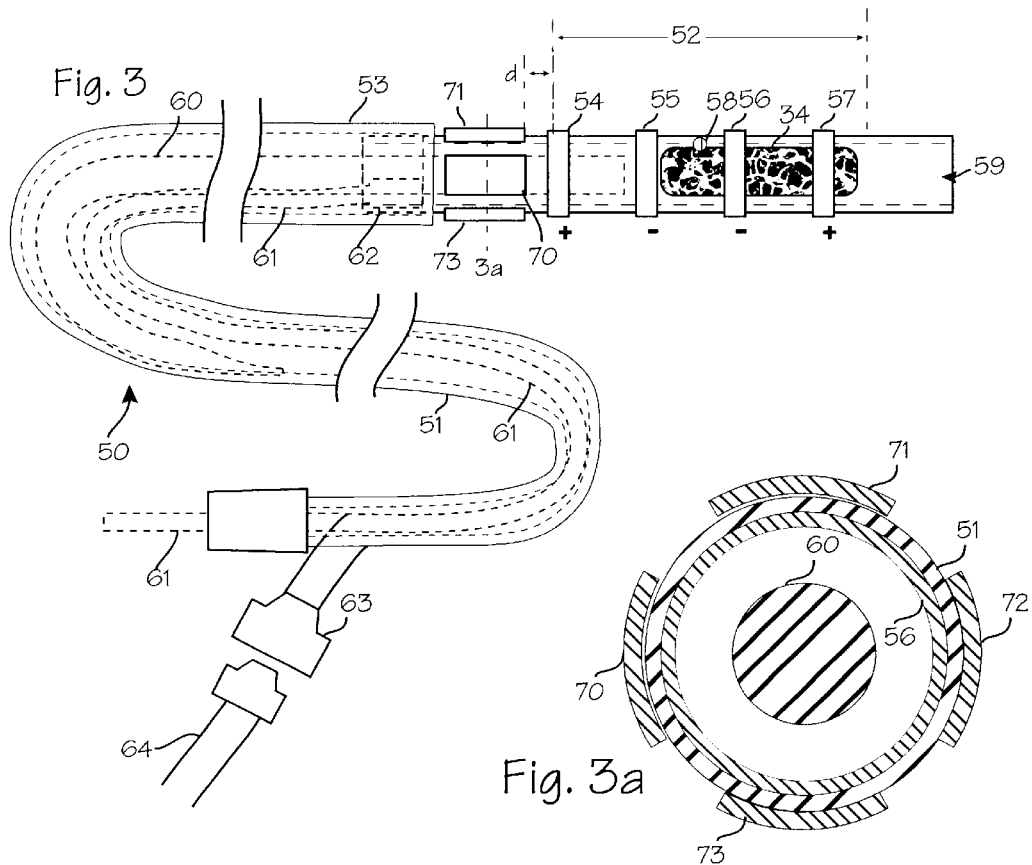
Fig. 3
Fig. 3a
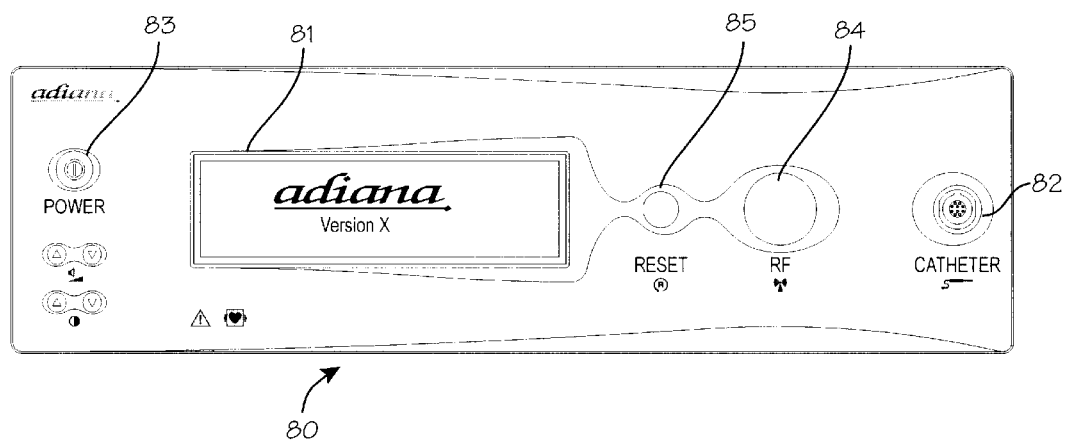
Fig. 4

CATHETER PLACEMENT DETECTION SYSTEM AND OPERATOR INTERFACE

FIELD OF THE INVENTIONS

The inventions described herein relate to catheters and other devices adapted for insertion into lumens in the body, and in particular to those catheters for which proper operation requires confirmed contact between the catheter and a body lumen.

BACKGROUND OF THE INVENTIONS

The catheter placement system and operator interface described below are intended to facilitate placement of catheters into body lumens. We have developed a catheter for treating the ovarian pathway of women. This catheter is described in U.S. Pat. No. 6,309,384, and provides two pairs of bipolar ring electrodes on the distal tip of a catheter, and an occlusive mass within the distal tip. The catheter is used to occlude ovarian pathway by inserting the distal tip into the ostium, seating the distal tip firmly within the ovarian pathway, applying RF energy to the ovarian pathway through the electrodes to injure a segment of the ovarian pathway, and then ejecting the occlusive mass into the ovarian pathway (in the injured segment). The procedure is highly effective. The ease of use of the system can be enhanced, and the certainty of property placement can be more easily determined, with our new placement detection system and operator interface. Additionally, several procedural safeguards can be implemented through the interface.

SUMMARY

The methods and devices described below provide for more certain operation of catheters, such as our ovarian pathway treatment catheters, into lumens of the body. The catheter itself is fitted with a circumferential array of electrodes, which, when placed in a circuit for which impedance or resistance is monitored, have varying effect on the measured impedance or resistance depending one whether the electrodes are in contact with the luminal tissue of the ovarian pathway or not. The impedance or resistance also varies, in a predictable manner, with the degree of contact between the electrodes and the luminal tissue of the ovarian pathway. An operator interface is provided which communicates the impedance measurement information to the operator in an intuitive display, and permits the operator to control the catheter. Additionally, a control system is provided which controls the catheter to prevent certain undesired modes of operation, and to control operation of the catheter in the event of an interruption in proper operation. Finally, an RF circuit which is specially adapted to supply the necessary RF signals and measure the impedance or resistance of tissue in contact with the electrodes, given that the circuit includes otherwise overwhelming capacitive impedance inherent in the structure of the catheter (which is several feet long, and includes the many wires necessary to supply and sense the electrodes running in close proximity in the necessarily slender catheter).

BRIEF DESCRIPTION OF THE DRAWINGS

FIG. 3 illustrates a catheter with several ring electrodes which are supplied with electrical energy from a RF generator.

FIG. 3a shows the cross section of the catheter in the region of the position detection electrodes FIG. 4 illustrates the control box which presents the user interface to be used in conjunction with the catheter of FIG. 3.

DETAILED DESCRIPTION OF THE INVENTIONS

Figure 1:
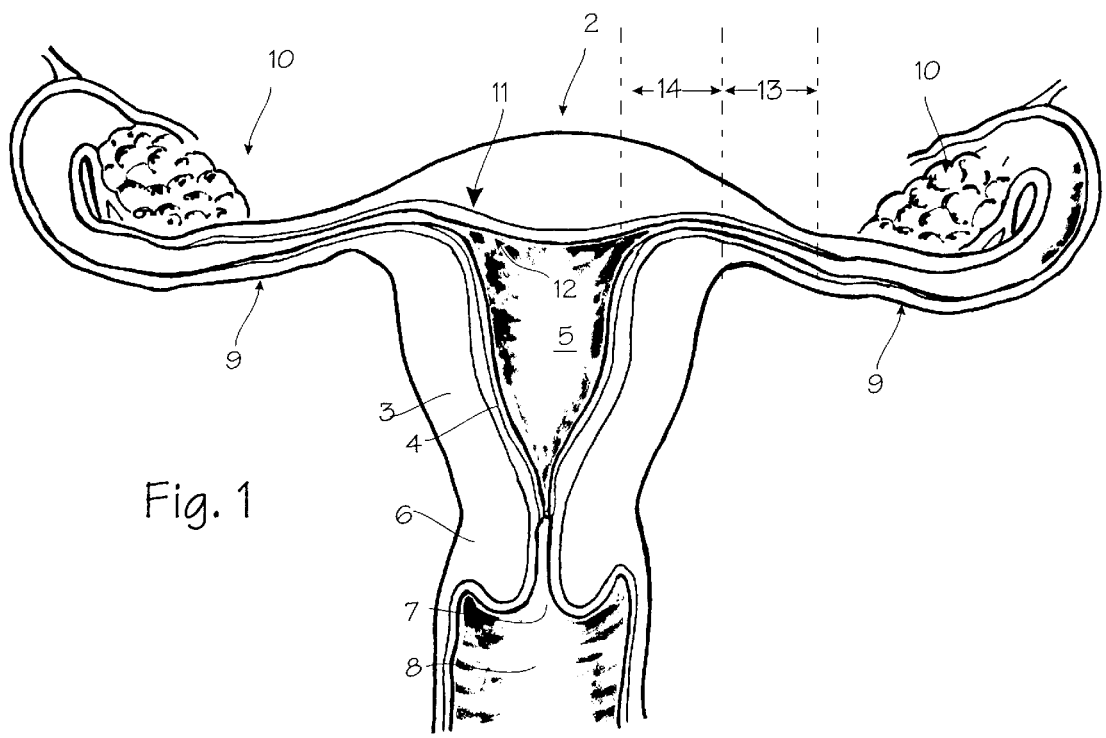
FIG. 1 is a partial view of the female reproductive system.
Figure 2:
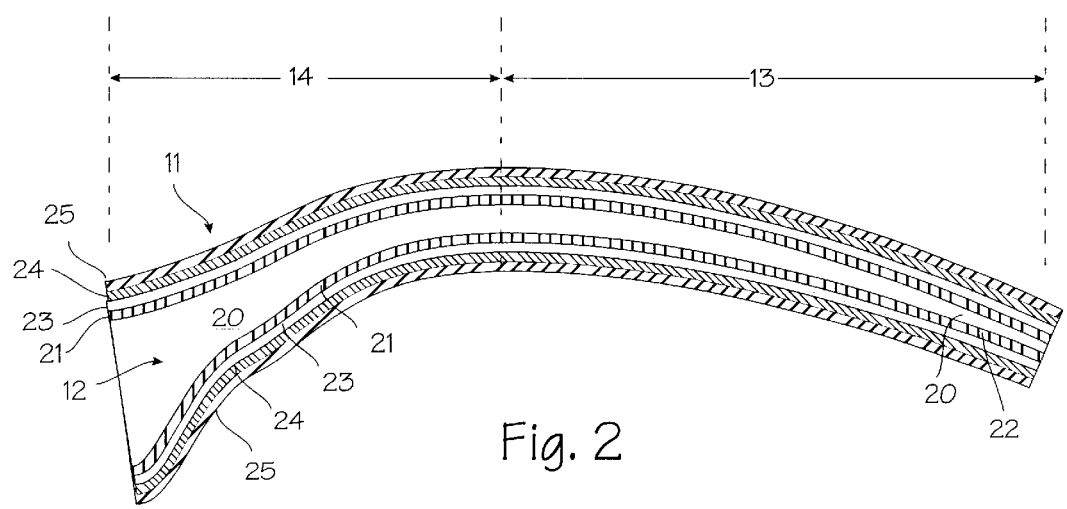
FIG. 2 is a cross section of the utero-tubal junction of the female reproductive system.

FIGS. 1 and 2 illustrate the environment in which the catheter placement devices and methods have been developed. The catheter is designed and intended to create a uniform lesion along a short length of the ovarian pathways of a female patient, and the challenges of this procedure are illustrated in the following figures. FIG. 1 shows some of the major elements of the female reproductive system. The uterus 2 is an organ of the female pelvis that has the shape of a pear. It consists of a thick muscular coat, the myometrium 3, a cavity having an inner mucosal lining of variable thickness called the endometrium 4, and a cavity referred to as the uterine cavity 5. The cervix 6 defines the cervical canal 7 which is an inferior opening to the vagina 8. The fallopian tube (or ampulla) 9 is a hollow organ that connects the uterus to the ovary 10. The ovary 10 is the organ that produces one or more eggs during every cycle of a woman's reproductive life. In the human female reproductive system, there is one uterus, two fallopian tubes and two ovaries (under normal conditions). The site where the fallopian tube and uterus connect is called the utero-tubal junction 11. It is a section of tubular shape of about 10 mm in length. Its inner diameter in the resting position is less than 1 mm, but when gas or liquid is pushed through the uterus and tubes, the diameter of the utero-tubal junction may stretch up to about 2 mm. The utero-tubal junction provides a transition between the uterus and the fallopian tube, and the area of transition from the chamber of the uterus to the lumen of the utero-tubal junction is referred to as the ostium or cornu (marked with item number 12). The area of transition between the ostium and the isthmus 13 of the fallopian tube is referred to as the interstitial portion (marked as item 14). The ostium, utero-tubal junction, interstitial portion, isthmus and fallopian tube are part of a pathway leading from the ovaries to the uterus, and this pathway is sometimes referred to as the uterine tube. For the sake of clarity we introduce the term ovarian pathway to denote the entire passageway through which the ova pass when transiting from the ovaries to the uterine cavity.

FIG. 2 shows the utero-tubal junction 11, including the ostium 12, the isthmus 13, and the interstitial portion 14. The cross section shows the layers of tissue that make up the utero-tubal junction. The lumen 20 passes through the fallopian tube, and this lumen is lined with a layer of mucosal tissue consisting of epithelium 21 and lamina propria 23. Within the fallopian tube, this layer of mucosal tissue is referred to as the endosalpinx, indicated as item 22. The layer of tissue under the epithelial layer is the lamina propria, indicated as item 23. The lamina propria is surrounded by a layer of circular muscle 24 which is surrounded by layer of longitudinal muscle 25. The longitudinal muscle layer may be surrounded with a second layer of circular muscle. The first circular muscle layer 24 typically comprises about 10–14 layers of muscle cells. One aspect of the our treatment method, described in our prior patent, is the extent to which each of these layers is damaged prior to insertion of an occluding plug. The desired damage is created by a catheter with several ring electrodes which are supplied with electrical energy from a RF generator.

FIG. 3 illustrates a catheter adapted for use with the system. The catheter 50 includes a catheter body 51 with a wounding segment 52 comprising a short tubular extension slidably mounted within the distal tip 53 of the catheter. The distal tip of the catheter body extends over the proximal end of the tubular extension for a short length of 2–25 mm, which is sufficient to firmly hold the tubular extension during use. Four ring electrodes 54, 55, 56 and 57 are aligned along the outer surface of the wounding segment. One or more temperature sensors 58 are mounted on the wounding segment. The distal tip and wounding segment are about 55 mil in outer diameter. The wounding segment in the RF embodiment is about 6 to 8 mm long, and the electrodes are ring electrodes which are about 0.037 to 0.050 inches wide (measured along of the longitudinal axis of the catheter) and wrap around the catheter. One or more foam plugs 34 are stored within lumen 59 the catheter body, and are shown housed within the wounding segment. By arranging the electrodes with the energized or hot electrodes 54 and 57 on the distal and proximal ends of the wounding segment, with the ground electrodes 55 and 56 situated between the hot electrodes, a long and shallow lesion may be produced in the ovarian pathway when the electrodes are energized appropriately. The converse pattern of ground electrodes located on the distal and proximal ends of the wounding segment with energized electrodes located between the ground electrodes may also be used to create the desired long and shallow lesion.

The plugs may be compressed to fit into the lumen in the wounding segment of the catheter. A holding rod 60 is disposed within the catheter body 51, fixed longitudinally within the catheter body at any point proximal to the wounding segment (it may be secured by gluing or heat sealing a proximal segment of the holding rod to the inner wall of the catheter body) which permits adequate pullback of the wounding segment to release the plug. A pullwire 61 is secured to the proximal end of the wounding segment by attachment of the boss 62 on the distal end of the pullwire. The pullwire extends proximally from the wounding segment to the proximal end of the catheter body. The pullwire 61 can be manipulated by hand from the proximal end of the catheter to pull the wounding segment proximally within the catheter body. The holding rod 60 maintains the plug (or plugs) in position within the ovarian pathway while the wounding segment is pulled proximally, thereby ejecting the plugs from the distal tip of the catheter without moving them relative to the wounded segment of the ovarian pathway after initial positioning (and also without moving the catheter body relative to the patient). Electrical wires which supply RF power to the electrodes may run the through the lumen of the catheter body alongside the pullwire or they may be housed within the catheter body, and an electrical connector 63 is supplied on the proximal end of the catheter to connect the wires in the catheter to the RF power supply through cable 64. The cable is provided in a length that allows for convenient placement of the control box, and may typically be three to six feet in length.

In use, the catheter is inserted into the uterus transcervally, and the distal tip of the catheter is navigated into the ovarian pathways, until the wounding segment is stationed at the desired point along the ovarian pathway (the utero-tubal junction is our preferred location for the wound and the plug placement). Surgeons may view the placement with an endoscope or hysteroscope, and/or placement within the pathway can be confirmed with fluoroscopy or ultrasound. Placement of the catheter may be accomplished blindly, using tactile feedback only. Once the wounding element is in place, the appropriate wound may be created by application of power limited so as to destroy the epithelial layer/endosalpinx in the area of plug placement, yet avoid unwanted physiological reactions. After wounding the ovarian pathway, the wounding segment is withdrawn by pulling the pullwire proximally while holding the catheter in place. This ejects the plug without need for relative motion between the plug and the wound after the operator has positioned the catheter for use.

Proper placement of this catheter within the ovarian pathway is important, and is ensured with position detection electrodes on the catheter of FIG. 3, which are used in conjunction with the user interface presented through the control box shown in FIG. 4. Referring again to FIG. 3, several electrodes 70, 71, 72 (hidden in this view) and 73 are placed around the outside circumference of the catheter to form a position detection array (PDA). As shown in FIG. 3a, which is a cross section of the catheter in the region of the position detection electrodes, the electrodes 70, 71, 72, and 73 are evenly spaced around the outer surface of the catheter, over the tube 51. The four electrodes are dispersed circumferentially about the catheter, such that each of the four electrodes is centered at approximately a 90° angle from the adjacent electrodes. The electrodes are curved to a diameter conforming to the outer diameter of the catheter, are about 0.010–0.030" long, about 0.006–0.012", preferably 0.009" across, and span about 60° to 90° of the circumference of the tube. These electrodes are connected to an AC or RF generator and impedance measurement circuit, so that the impedance of the circuit established by these electrodes and one of the ring electrodes can be measured.

The impedance changes with the degree of contact between the various electrodes of the catheter and body tissue. Regardless of the distention medium used during the procedure, the impedance will change measurably and predictably when the electrodes change from suspension in the medium and contact with the body tissue, and also when the force of contact varies. By detecting this impedance change, contact between the ovarian pathway and the catheter can be ascertained. The distance D between the array of the position detection electrodes and the wounding segment is chosen to correspond to the desired depth of placement of the wounding segment within the ovarian pathway. Using average anatomy as a basis, the distance D is set at about 1.5 mm, so that with a catheter of diameter about 1 to 2 mm, the wounding segment will be located in the interstitial portion of the ovarian pathway when the position detection array is seated in the ostium. If desired, a second array of position detection electrodes may be placed proximal to the illustrated array. This array can be used to detect contact between it and the ovarian pathway. When it is desired to place a treatment segment in any ostium without inserting too far into the ostium (as here, where placement deep inside the fallopian tubes is not desired), this second position detection array will enable the system to detect over-insertion, and confirm that over-insertion has not occurred, and prevent application of wounding energy when the wounding segment is located too deeply within the ovarian pathway. Thus, this second detection array should be located a distance proximal to the treatment segment such that contact, given the diameter of the second position detection array, between the second position detection array and the treatment segment would be indicative of over-insertion. This second position detection array can be operated in the same manner as the depicted position detection array. Additional position detection arrays may be placed elsewhere on the catheter, and may be particularly useful in determining the depth of insertion of the catheter in the ovarian pathway or other lumens of the body, particularly where the desired depth of placement may vary from procedure to procedure. These additional position detection arrays may also be placed on the treatment segment or distal to the treatment segment, and may be used by the system or the system operator to select which of several treatment electrodes, or other treatment means, to activate in the course of treatment.

Each of the position detection electrodes may be placed to correspond to a discernible aspect of the patient, meaning that once inserted into the patient, the surgeon operating the device can discern which electrode is facing upward relative to the operating table (anterior of the patient, since the patient is typically placed lying, face up, on an inclined table), and which is facing downward relative to the patient (posterior of the patient), and which are facing left and right relative to the patient. This is helpful to assist the surgeon in manipulating the catheter in response to the user interface. However, it is quite easy to manipulate the catheter without any indication of the orientation of the electrodes, since random manipulation (wiggling) of the catheter to encourage distal movement into the ovarian pathways to obtain the desired display (illustrated below) has proven adequate for secure and correct placement.

FIG. 4 illustrates the control box which presents the user interface to be used in conjunction with the catheter of FIG. 3, while the following figures illustrate various aspects of the interface. The control box 80 includes the interface display 81, a power and signal connector 82 for providing impedance measuring signals and treatment power the catheter, as well as receiving impedance signals from the position detection electrodes. A main power switch 83 controls power to the control box for powering of the display, indicators lights, any desired audio signals, and the catheter. A catheter power switch 84 controls the provision of treatment power to the electrodes 54, 55, 56 and 57 shown on the catheter in FIG. 3. A reset switch 85 controls re-initiation of the system, needed in instances described below. As shown in this embodiment, each switch is provided in the form of a pushbutton toggle switch combined with an indicator light. In FIG. 4, the display is merely the startup screen which indicates that the system is powered and the software and hardware necessary to operate the system have successfully initialized or booted. The control box houses electronics and a computer system for interpreting signals from the position detection electrodes, driving the display, receiving operator input and controlling the catheter accordingly.

Figure 5:
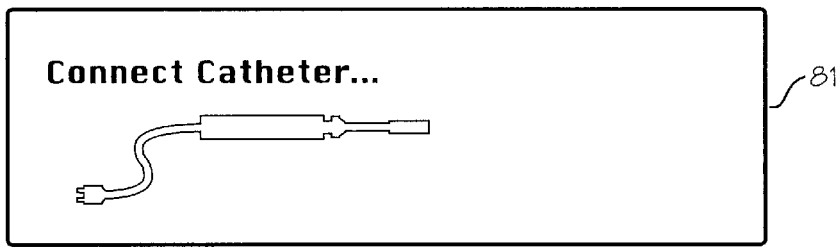
FIG. 5 illustrates a display provided by the control box during operation of the system.
Figure 6:
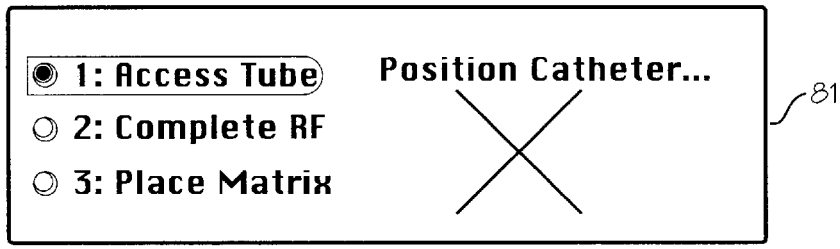
FIG. 6 illustrates a display provided by the control box during operation of the system.

FIGS. 5 through 13 show various text and text prompts, icons and icon prompts, and other display elements produced by the control box. The display illustrated is designed for an inexpensive, low resolution, two-tone LCD display, but the display can be implemented with simpler displays or more sophisticated displays. In FIG. 5, the display field is driven by the computer housed within the control box to display an initial prompt to the operator. In FIG. 6, the system displays a series of status statements and prompts. The prompts "Access Tube," "Complete RF," and "Place Matrix" are displayed simultaneously, as prompts and status statements. Initially, the background field and radio button display (or any other form of emphasis) is produced behind the "Access Tube" prompt as an indicator that this step must be accomplished, and that the system is ready to accept input from the catheter and provide a corresponding display. At this point, the surgeon will be inserting a catheter transcervically toward and into an ovarian pathway of a patient. (The surgeon may view the insertion through a hysteroscope or any other means, or may rely solely on the display. Given the anatomy of the uterus and ovarian pathway, there is no chance for an ambiguous indication from the display, and it would be cumbersome to provide direct visualization of the catheter tip after insertion in the ovarian pathway. Nonetheless, direct visualization could be provided by adding endoscopic capability to the catheter.)

Figure 7:
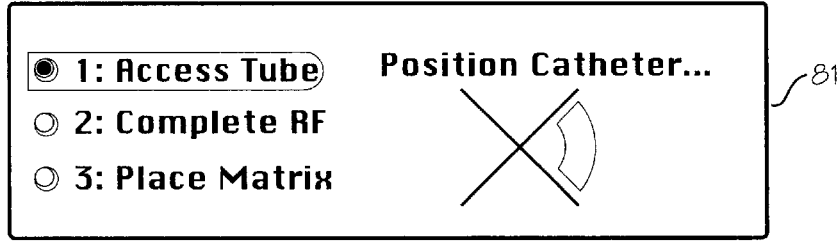
FIG. 7 illustrates a display provided by the control box during operation of the system.
Figure 8:
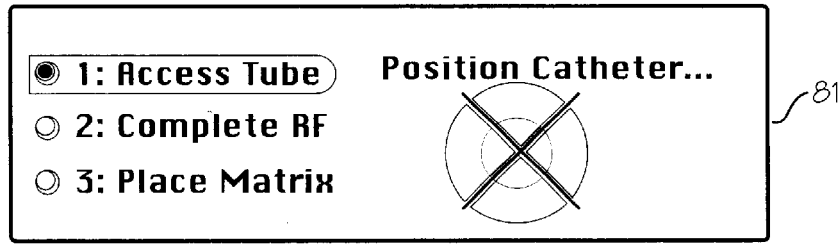
FIG. 8 illustrates a display provided by the control box during operation of the system.

During insertion, while the catheter tip is surrounded by the distension medium or voids within the insertion pathway, the measured impedance will be characteristic of this (typically, a very high impedance will be sensed, compared to the impedance sensed from an electrode in contact with the ovarian pathway). When contact is made between one or more position detection electrodes and body tissue, the detected impedance will change, and the display is altered to indicate contact. FIG. 7 shows the display provided when a position detection electrode makes contact with the tissue within the ovarian pathway. The display includes an image area for display of four circularly arranged quarter-circle icons corresponding to the four circularly arranged position detection electrodes distributed around the catheter tip. As each electrode makes contact with tissue in the ovarian pathway, a corresponding quadrant of the image area is filled or marked by the display with the arcuate icon. Illustrated in FIG. 7 is the case where only one electrode is in contact with tissue of the ovarian pathway. It is clear from this display that the catheter tip is not seated in the ovarian pathway, because only one electrode is providing an impedance measurement indicative of contact. FIG. 8 shows the display which indicates that all four position detection electrodes have made contact with the ovarian pathway. This indicates that the entire catheter tip is disposed in the appropriate position in the ovarian pathway, as ensured by the distance set between the position electrode array and the wounding segment (see FIG. 3).

Figure 9:
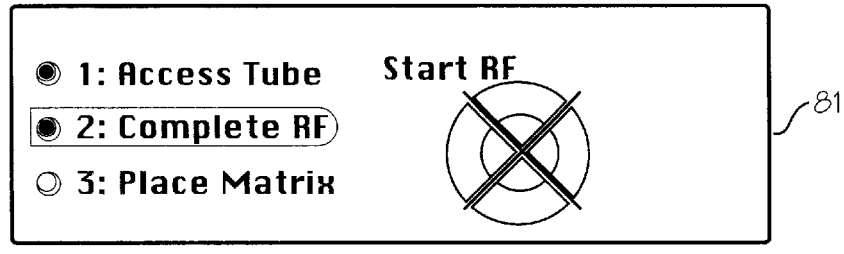
FIG. 9 illustrates a display provided by the control box during operation of the system.

In FIG. 9, the display indicates to the surgeon that the catheter is properly positioned and that wounding energy may be applied through the ring electrodes. The control system has operated to permit energy to be applied to the patient. In this manner, both the surgeon and the system must be in agreement as to proper placement of the system before wounding energy is applied. To apply energy, the surgeon presses the catheter power switch 84 (see FIG. 4), and the system applies RF energy through the ring electrodes, for a predetermined period. The control system is programmed to analyze input from position detections means described below, determine when full contact has been established between the catheter and the fallopian tube, adjust the display to inform the operator that contact has been established, and enable the application of RF energy upon manual input from the operator only when full contact is established. If a second proximal position detection array is used on the catheter, the system may be programmed to analyze input from the second position detection array, and disable or prohibit application of RF energy if contact is sensed with the second array. The system may be further provided with an override capability, so that a surgeon may override the system prohibition against application of RF energy prior to sensing contact, by providing an additional input means or control button on the face of the control box. This may be useful in cases of a typical anatomy. (Alternatively, the control system may be programmed to automatically initiate application of RF energy if the sensed impedance for all electrodes meets a very low threshold of, for example, $1000\Omega$, which is deemed unequivocal indicate of proper positioning of the wounding segment.)

Figure 10:
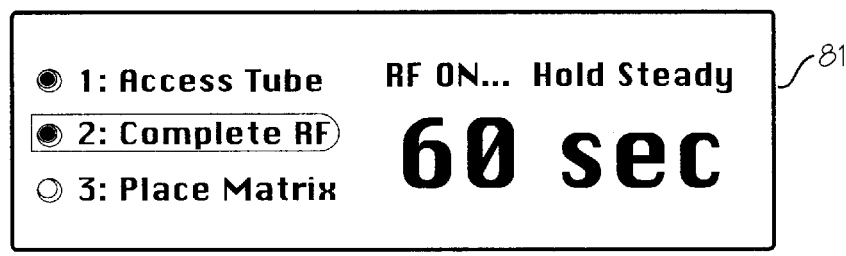
FIG. 10 illustrates a display provided by the control box during operation of the system.
Figure 11:
FIG. 11 illustrates a display provided by the control box during operation of the system.

FIGS. 10 and 11 show the response of the system to the application of RF energy to the catheter. The system will apply a preset amount of power for a preset time period (0.5 to 3W, for 60 seconds in the embodiment shown) and present a countdown counter to the surgeon. FIG. 10 shows that the control system has started applying power for the sixty second period, and has presented a countdown counter on the display. FIG. 11 shows that the system has counted down through the sixty seconds.

Figure 12:
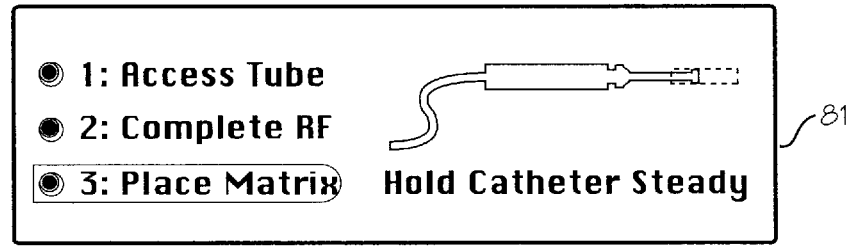
FIG. 12 illustrates a display provided by the control box during operation of the system.

Through experimentation, we predetermine the power that must be applied to the fallopian tubes and the time that this power must be applied, to ensure fallopian tube occlusion. While it may be permissible to apply energy for longer periods, shorter periods of power application may result in a higher probability of failure. In FIG. 12, the system has applied RF power to the catheter for 60 seconds, and has observed contact for the entire sixty seconds, and therefore indicates that the plug or matrix (see FIG. 3) may be ejected from the catheter. It does this by highlighting the text of the "Place Matrix" prompt, and provides the additional cautionary message to hold the catheter steady to ensure that the catheter and plug do not move relative to the wounded portion of the ovarian pathway.

The control system is programmed to continuously monitor the position of the catheter during treatment, and, if contact between the catheter and the fallopian tube is lost, provide a clear indication to the operator that contact is lost and discontinue application of treatment energy. Additionally, the control system is programmed to prompt the operator to reposition the catheter and reinitiate treatment. When reinitiating treatment, the control system will not allow the operator to resume an interrupted treatment period, but will restart a complete new treatment period. Thus, if contact is interrupted after a partial treatment, the system will prompt the operator to replace the catheter and restart treatment, and will reset the treatment timer to the full 60 second treatment period. It will not present the operator with an opportunity to resume the treatment for the remaining time of the interrupted treatment period.

Figure 13:
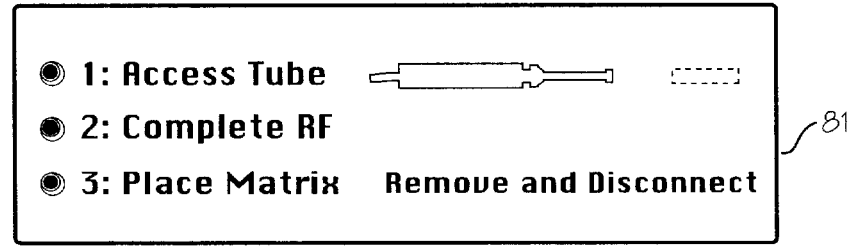
FIG. 13 illustrates a display provided by the control box during operation of the system.

In FIG. 13, feedback from the catheter indicates that the plug has been ejected, so that the catheter may be removed. The catheter is then discarded, because it is not easily sterilized in the field, nor is it easily reloaded with a plug without special equipment and controls. Typically, a patient requiring occlusion of one fallopian tube also requires occlusion of the other, so the process is repeated on the other fallopian tube with a second catheter.

Figure 14:
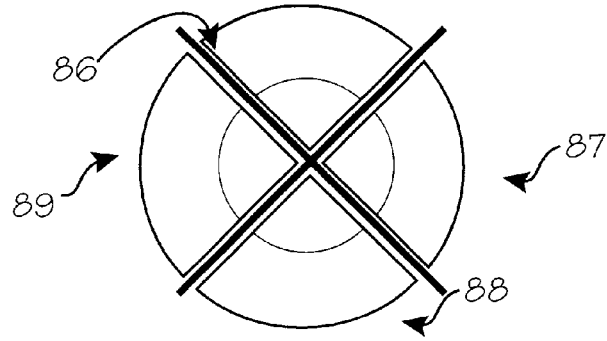
FIG. 14 illustrates an iconic display for communicating the state of catheter contact to the user.

FIG. 14 shows the contact indicating portion of the display shown in FIGS. 7 and 8. A portion of the display is divided into four quadrants 86, 87, 88 and 89 and these four quadrants correspond to the four electrodes in the position detection array on the catheter. When placed into the patient, with the patient oriented in a standard manner (face up, slightly inclined), the catheter is oriented so that one electrode is facing forward relative to the patient (the handle of the device may be formed to facilitate appropriate orientation, and the electrodes or catheter may be marked to identify which electrodes will be assumed to correspond to the patient cardinal points). If no provision is made for correlating specific electrode cardinal points (up, down, front and back relative to the patient) to the quadrants of the display, then the surgeon can quickly test movement of the catheter and display response to determine which side or sides of the catheter are not in contact with the ovarian pathway.

Figure 15:
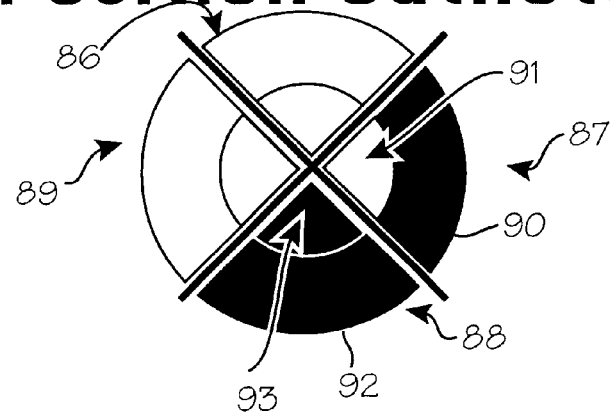
FIG. 15 illustrates an iconic display for communicating the state of catheter contact to the user.

Now referring to FIG. 15, once contact has been made between and electrode and the ovarian pathway, the system senses the impedance change, and alters the appearance in the associated display quadrant. If contact is light, the outer quarter circular or annular area 90 will be altered, for example highlighted or filled with contrasting color as shown in quadrant 87, while the inner circular quadrant 91 will not be highlighted. If contact is tight, both the associated outer circular area 92 and the associated inner circle area 93 will be altered, as appears in quadrant 88. The display as shown here indicates to the surgeon that one electrode is in light contact, and an adjacent electrode is in tight contact, with the ovarian pathway. This indicates that the catheter tip is resting on the ostium, perhaps, or askew within the ovarian pathway, or only partially inserted into the ovarian pathway. In response, the surgeon may manipulate and steer the catheter tip to further insert the distal tip or align the distal tip with the axis of the ovarian pathway. When the catheter is placed so that all position detection electrodes are tightly in contact with the ovarian pathway, the contact indicating portion of the display will appear as in FIG. 16.

To generalize the quadrant based display, in the case that a different number of electrodes are used, the contact indicating portion of the display can be driven to represent any number of radial segments (like pie slices) which correspond to the number of electrodes used, and these radial segments can be illuminated or filled partially or fully depending on the degree of contact sensed by the system. Other iconic or text based displays can be used, including a series of vertical or horizontal bars which change length with impedance measured. In its simplest embodiment, a single visual or audible indication (a green light or a chime) could be used to indicate that all position detection electrodes are in contact with the fallopian tube. The secondary indication of tight contact can also be accomplished with varying visual indication, including alterations in the brightness of the display areas associated with electrodes, or changes in color of those areas. So, for example, the inner and outer radial or annular segments may be replaced by a single radial segment that is illuminated in one color, brightness, opacity, etc. to indicate light contact and a second color, brightness, opacity, etc. to indicate tight contact.

The system provides RF measuring power to the electrodes and measures the impedance or resistance of the tissue in contact with the electrodes (the tissue impedance in the fallopian tubes is almost entirely resistive, and reference to impedance herein includes both resistance and impedance). The system is programmed to detect when the impedance is in the range of impedance experimentally determined to indicate contact with the ovarian pathway (as opposed to contact with the distention medium or air), and produce a display indicating that contact has been made. In a simple implementation, in the electrical circuits which we use and the size of electrodes, and the length and location of the many wires in the catheter, an impedance in the range of zero to 30,000Ω is indicative of contact, while impedance in a range of 6 KOhm to 12 Kohm is indicative of tight contact with an exertion of slight pressure by the electrodes against the ovarian pathway. In contrast, the measured impedance in air is infinite, and the measured impedance in a distension medium such as glycine is about 50 Kohm (which indicates some slight conductivity due, perhaps, to traces of blood and ionic fluids in the glycine). While these numbers apply to the devices we have built, the numbers required for other implementations of the catheter and the RF circuitry may be different, but may be experimentally determined. The preferred distention medium is non-ionic such as glycine, in which case the impedance measured at the electrodes will decrease upon contact with the ovarian pathway. However, ionic distension mediums may be used.

Variations in patient physiology, distention media properties, slight variations in catheters built to the same specifications, and the tightness of placement may impart variations to the impedance measurements. To account for such variations in impedance measurements, the computer system is programmed with software which analyzes the several impedance measurements and compares the measurements in order to determine whether secure contact has been achieved between the PDA electrodes and the fallopian tube. We refer to this system as a dual threshold scheme. In this scheme, measured impedance from each PDA electrode must meet or exceed a first threshold, and the measured impedance from all contacts must fall within a predetermined range of values. When these conditions are met, the display is manipulated to indicate that the catheter is properly seated. Thus, the computer system within the control box is programmed to determine that a particular position detection electrode is in contact with the ovarian pathway, and alter the display accordingly, when the impedance measured at the particular electrode falls into a first predetermined range and the impedance measured at all electrodes falls within a second predetermined range. The computer system can be programmed to provide an additional indicate of the tightness or degree of contact when the impedance measured at all electrodes falls within a third predetermined range (typically, a smaller range than the second range, which is interpreted to indicate tighter contact).

Figure 16:
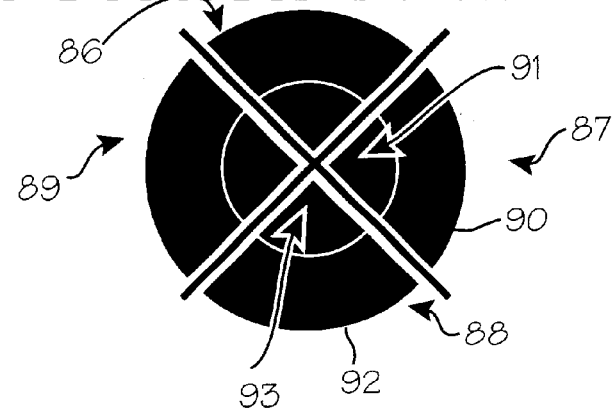
FIG. 16 illustrates an iconic display for communicating the state of catheter contact to the user.

First, if the measured impedance at one position detection electrode is greater than a predetermined level (we use 24,000Ω for our particular catheter construction, but a threshold in the range of about 20 Kohm and 30 Kohm may be used), the system will interpret this as non-contact, regardless of the impedance measured at other position detection electrodes. If the measured impedance at the position detection electrode with the lowest impedance is lower than the predetermined level (24,000 ohms), and the impedances of all four electrodes are within a predetermined range (17,000 ohms), then the system will interpret this as light contact between the catheter and the fallopian tube. If the measured impedance at the position detection electrode with the lowest impedance is lower than the predetermined level (24,000 ohms), and the impedances of all four electrodes are within a narrow predetermined range (4,000 ohms), then the system will interpret this as tight contact between the catheter and the fallopian tube. (The method of determining contact by first determining a threshold for each electrode, and then determining if all electrodes fall within a range of impedances can be implemented in other forms. For example, If the measured impedance at one position detection electrode (the electrode indicating the lowest impedance) is lower than the first predetermined level, but all electrodes are not within predetermined range (we use 17,000Ω), then the system will interpret this as non-contact, no matter how low the impedance is for that particular electrode. If the measured impedance at one position detection electrode is lower than the predetermined level, and the measured impedance of the one position detection electrode and the electrodes with the lowest impedance is within a broad predetermined range (we use 17,000Ω), then the system will interpret this as light contact between the electrode and the fallopian tube. If the measured impedance at one position detection electrode is lower than the predetermined level, and the measured impedance of the one position detection electrode and the electrode with the lowest impedance is within a narrow predetermined range (we use 4,000Ω), then the system will interpret this as tight contact between the electrode and the fallopian tube.) Correspondingly, the system will control the display to indicate that the position detection electrode is in light contact with the fallopian tube by creating a corresponding image on the display, when light contact is determined, and the system will control the display to indicate that the position detection electrode is in tight contact with the fallopian tube by creating a corresponding image on the display, when tight contact is determined. The display uses outer arcs or annular segments to indicate light contact and inner quadrants to indicate tight contact, as illustrated in FIGS. 15 and 16. The operation may be summarized in the following table:

| Measured Impedance | Impedance Ranges | Outer Arc | Inner Quadrant |
| --- | --- | --- | --- |
| Greater than 24,000 Ω | Any Range | off | off |
| Less than or equal to 24,000 Ω | greater than 17,000 Ω | off | off |
| Less than or equal to 24,000 Ω | between 4000 Ω and 17000 Ω, inclusive | on | off |
| Less than or equal to 24,000 Ω | less than or equal to 4,000 Ω | on | on |

In this table, the range refers to the difference between the electrode under analysis and the minimum impedance of all four electrodes, and is calculated by Range=abs[the minimum of the four PDA electrodes−the impedance of the current PDA electrode]. Thus, if the electrode under consideration measures less than 24,000Ω, and it is the lowest impedance electrode, then the system will interpret this to mean that it is in tight contact, regardless of how high the impedance is at the other electrodes. If the electrode under consideration measures an impedance of 23000Ω, but the lowest measured impedance is only 4,000Ω, then the system will interpret this as non-contact.

When all four electrodes indicate impedance less than 24,000Ω and variation amongst the electrodes is less than 17,000Ω will the system indicates light contact with all four position detection electrodes. Only when all four electrodes indicate impedance less than 24,000Ω and variation amongst the electrodes is less than 4,000Ω will the system indicate tight contact with all four position detection electrodes. The system is programmed to determine that tubal contact is complete when all four position detection electrodes meet the conditions for tight contact for at least about 200 milliseconds. All values for the impedance thresholds, ranges, and time periods are derived empirically for specific builds of catheters, and other values may be required for other builds. The values have also been derived for the fallopian catheters, and appropriate values can be empirically determined for catheters intended for use in other lumens and vessels of the body such as blood vessels, the chambers of the heart, and the esophagus.

The impedance measurement circuit drives the position detection electrodes with very low level, low frequency (3 Khz) RF current (this would also be considered a high frequency alternating current) between the selected electrode and ground. The voltage developed across the resistance of the position detection electrodes is amplified, filtered (to ignore the currently preferred 460 Khz treatment voltage, so that position detection and treatment can be performed simultaneously) and translated into a DC voltage signal and outputted to the control system. The control system software compares the voltage measurement with values stored in a lookup table in memory associated with the computer to determine the impedance measured between the electrodes. The output of the impedance measurement circuit is a voltage proportional to (or otherwise corresponding to) the measured impedance, and this output is received by the control system. The system drives the display to indicate that the contact is made, depending on the voltage output of the impedance detection circuit. We refer to the voltage, or any other measured parameter indicative of impedance, as an impedance signal.

Figure 17:
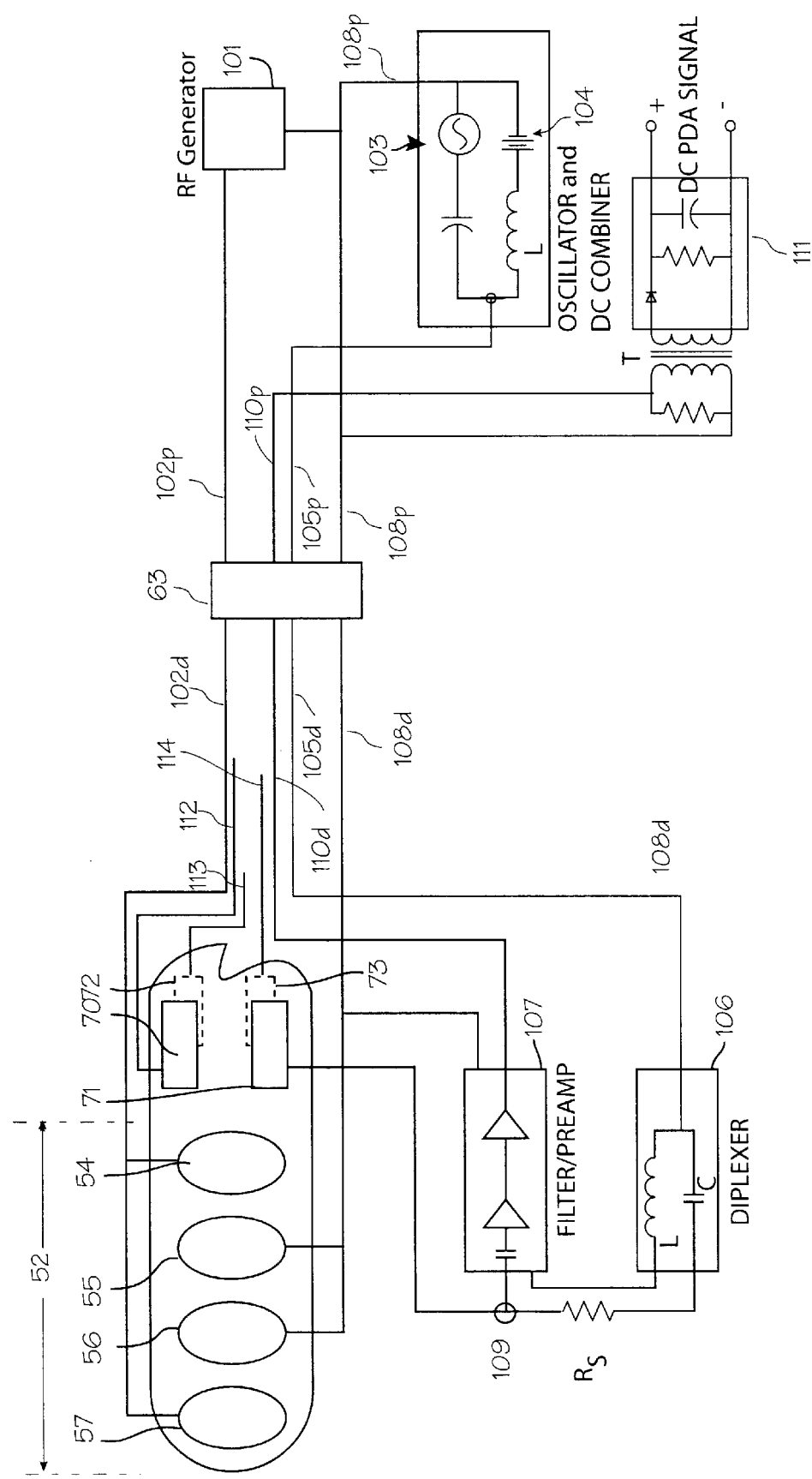
FIG. 17 shows a circuit adapted for measuring the impedance of the electrodes in the environment of use.

FIG. 17 shows a circuit adapted for measuring the impedance of the electrodes in the fallopian tubes. The circuit includes the various electrodes used for position sensing, the four electrodes used for treatment, a power supply for the impedance sensing, filters, preamps, and an envelope detector. The wounding segment 52, electrodes 54, 55, 56 and 57, and position detection electrodes 70 and 71 (as well as electrodes 72 and 73 which are shown in phantom in this view) are the same as those shown in FIGS. 3 and 3a. The treatment electrodes are provided with RF energy for treatment from an RF generating circuit 101 through conductor 102 (with distal and proximal portions 102d and 102p), which is not part of the impedance measuring circuit but may share elements such as ground and power supplies with the impedance measuring circuit. The RF generator provides RF power in the frequency range of 400 to 500 Khz.

An oscillator circuit 103 provides relatively low frequency RF current (1 to 30 KHz, preferably about 3 Khz) and the DC source 104 provides DC power through the single conductor 105p and 105d, through the diplexer 106. (We refer to conductors 105d and 105p as a single conductor, even though is comprises two sections separated by connector 63, to distinguish this structure from the alternative of using one conductor for RF and a second conductor for DC power, which would require two parallel conductors.) The DC current is passed to the filter/preamp 107 to power the filter/preamp, while the RF signal is passed through resistor $R_s$ to the position detection electrodes, through any body tissue overlying both the treatment electrode 55 and the position detection electrodes, to the treatment electrode, and from there to the remainder of the circuit. The circuit continues from the treatment electrode through conductor 108d and 108p (conductor 108p runs from the connector 63, while corresponding conductor 108d runs from the connector to the distal tip of the catheter), to system ground. The resistor $R_s$ along with whatever connects the position detector electrode and the proximal treatment electrode comprises a basic voltage divider. The filter/preamp 107 detects the voltage at the PDA electrode, at voltage divider tap 109, and transmits a corresponding signal through conductor 110, hand finally to the transformer T and envelope detector 111. The filter/preamp includes a high pass filter which removes any high frequency RF signal from the treatment current, so that the output is related solely to the voltage due to the signal from the oscillator. The filter preamp may be provided on the proximal side of the connector 63, and can be located on the circuit boards located within the control box, in which case the diplexer may be omitted in favor of discrete connections to appropriate power supplies for the filter/preamp and the PDA signal.

The envelope detector produces a DC voltage which corresponds to the voltage of the AC signal transmitted from the preamp. This voltage is in turn a function of the relationship between the impedance of circuit elements comprising the electrode 55, the position detection electrode 71, and whatever establishes the circuit between them (whether it be air, distension medium, the luminal wall of the fallopian tube). This function may be accomplished by an envelope detector and its many equivalents. The filter and amplifier take input from the voltage divider tap and serve (1) to isolate the envelope detector from the input and effect on voltage measured at $R_s$ that would otherwise result from the application of the high frequency, high voltage signal from the treatment energy supplied to the electrodes in the wounding segment and (2) to boost the AC signal so that the voltage signal seen by the envelope detector is not unduly affected by the cross talk due to the naturally high capacitance between the several wires running through the cable. The amplifier may be placed as close as practical to the electrodes, preferably distal to the connector 63, close to the body of the patient, and, if possible, just proximal to the electrode arrays so that it resides (when the catheter is in use) in the uterus or just outside the body of the-patient. The diplexer serves to (1) provide power to the filter and amplifier and (2) provide the PDA measurement signal to the PDA electrode through resistor $R_s$, and allows both to be accomplished through the single conductor 105d and 105p, but does not otherwise effect the signal provided from the voltage divider to the envelope detector. If the diplexer is omitted, separate conductors will be used for the distally located preamp and the oscillator signal, increasing the problem of inherent crosstalk between the many conductors in the cable and catheter. Each of the position detection electrodes is provided with it owns distinct impedance sensing circuit, so that the circuit components including the filter/preamp, transformer and envelope detector are provided for each position detection electrode, each set of components being connected to a position detection electrode via the conductors 112, 113 and 114.

In this implementation, the ring electrode 55 is used as a return electrode in circuit with the position detection electrodes, in a bi-polar arrangement where small RF current runs from the position detection electrodes to the ring electrode and thereon to the system ground. Thus it is the impedance of that part of the circuit spanning the gap between the ring electrode and the PDA electrode which is being measured in this embodiment. The circuit may be adapted so that impedance is measured between the various position detection electrodes, such that the position detection electrodes are arranged and energized in bipolar pairs, or such that electrodes are energized with the impedance detection signal sequentially, while surrounding electrodes are used as ground electrodes. The circuit may also be implemented using any of the ring electrodes used as return electrodes for the impedance detection circuit.

Figure 18:
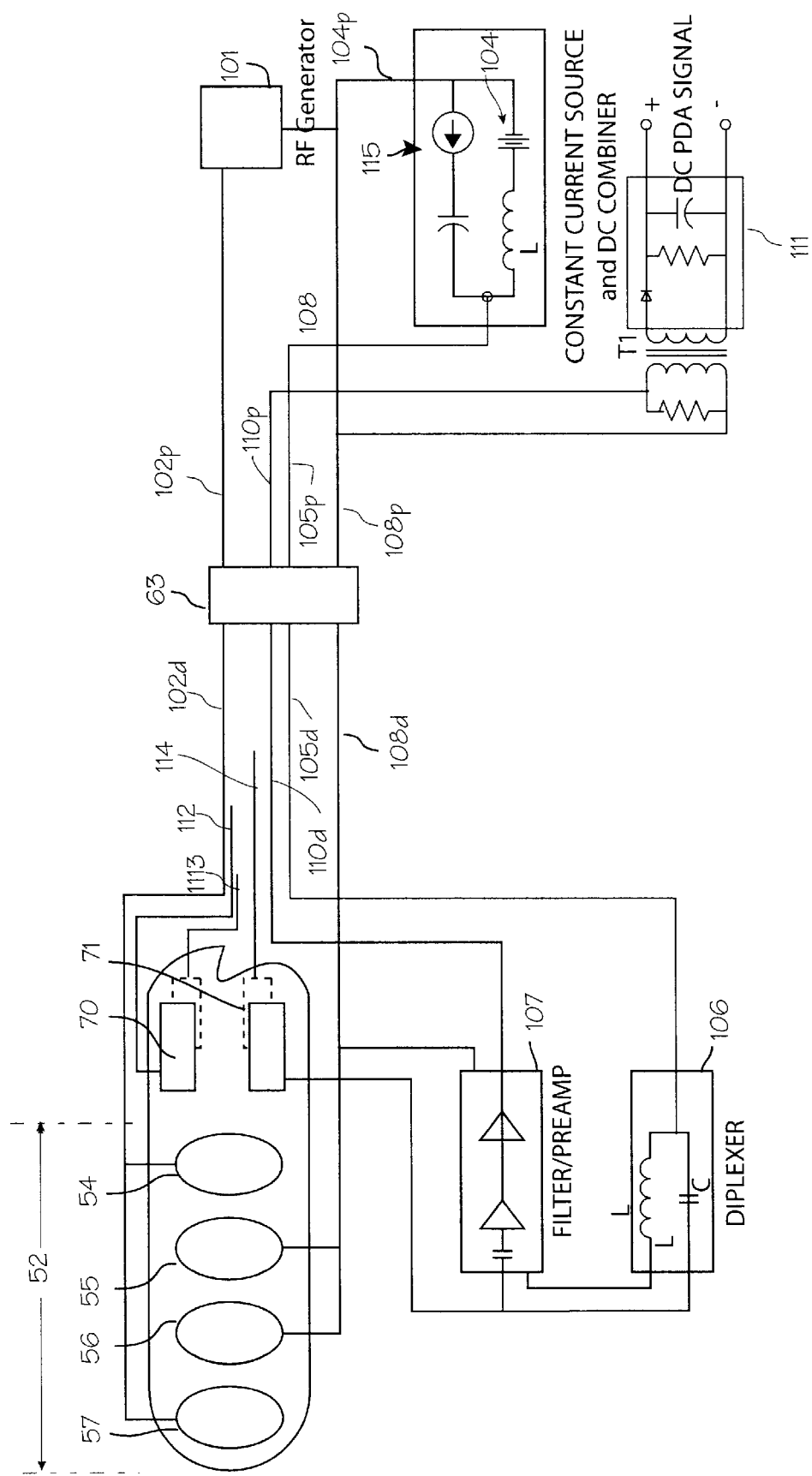
FIG. 18 shows another circuit adapted for measuring the impedance of the electrodes in the environment of use.

FIG. 18 shows another circuit adapted for measuring the impedance of the electrodes in the environment of use. The operation of this circuit is similar to the operation of the circuit of FIG. 17, but a constant current source is used in place of the oscillator of FIG. 17. The constant current source 115 provides current which does not vary with the impedance or resistance of the tissue encountered in the circuit. Instead, it adjusts its voltage in order to supply the same current regardless of the encountered resistance (to a limit, of course). The filter and preamp 107 senses the voltage at the PDA electrode, and outputs a corresponding amplified voltage to the transformer T and the envelope detector 111. The constant current source may be limited to range of 20 to 30 micro amps, preferably 25 micro amps, to avoid generation of excessively high voltages in the circuit which occur when the system is operated in highly resistive mediums such as air (that is, when the system is inadvertently operated outside the body).

Figure 19:
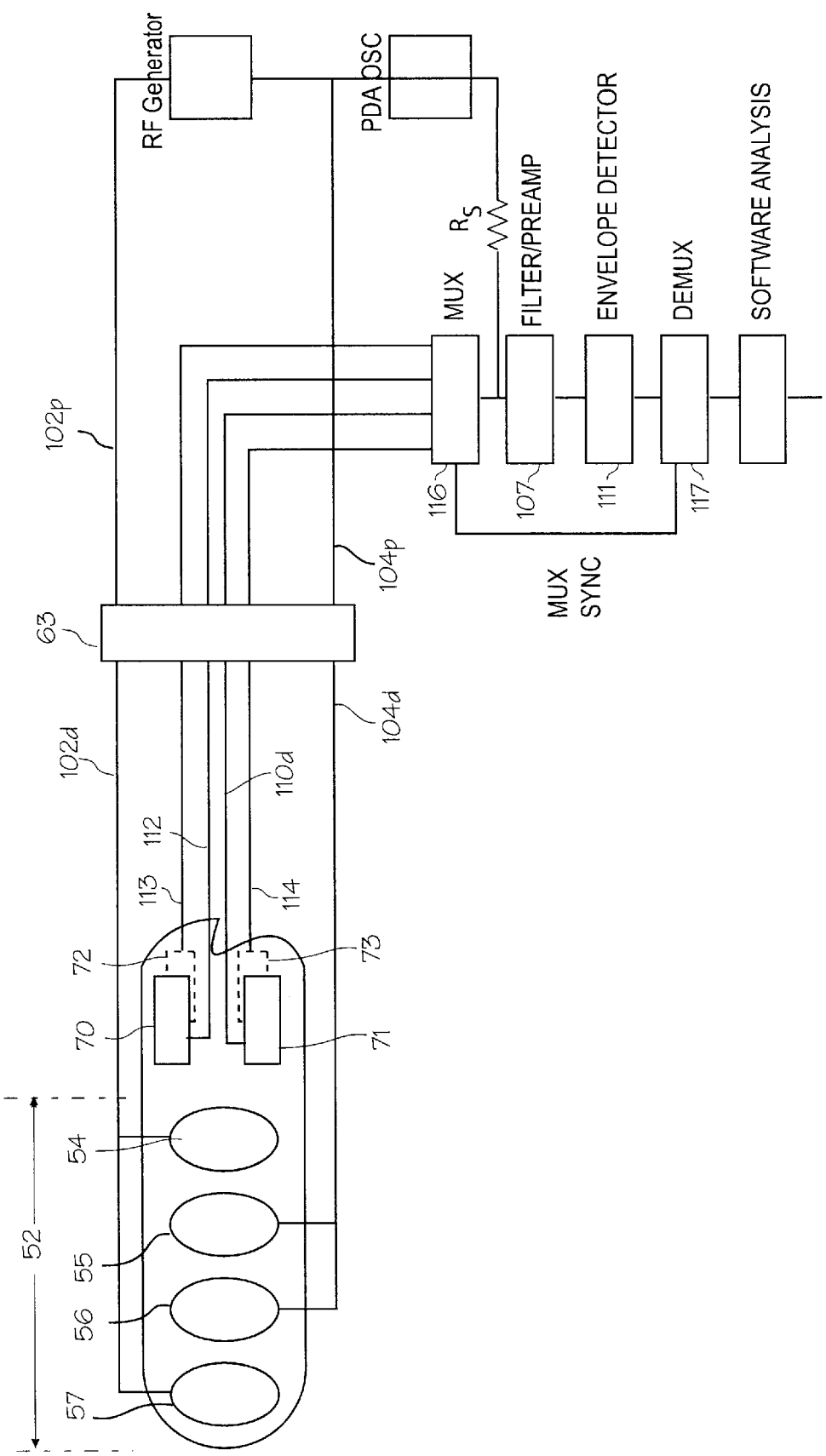
FIG. 19 illustrates the use of multiplexing circuits in the position detection circuitry.

FIG. 19 illustrates a variation of the circuit which may be applied to FIG. 17 or 18. In this illustration, the PDA electrodes are supplied with the RF detection signal, and the return signal is sensed, amplified and communicated to the software system through a single set of components located in the control box. The multiplexer 116 and demultiplexer 117 operate in conjunction with each other to multiplex the return signals into a single set of circuit analysis components such as the filter, preamp and envelope detector, and demultiplex them to provide four impedance signals, corresponding the four PDA electrodes, to the inputs of the software portions of the system. The demultiplexing function may also be accomplished through the software used to analyze the impedance signal.

Figure 20:
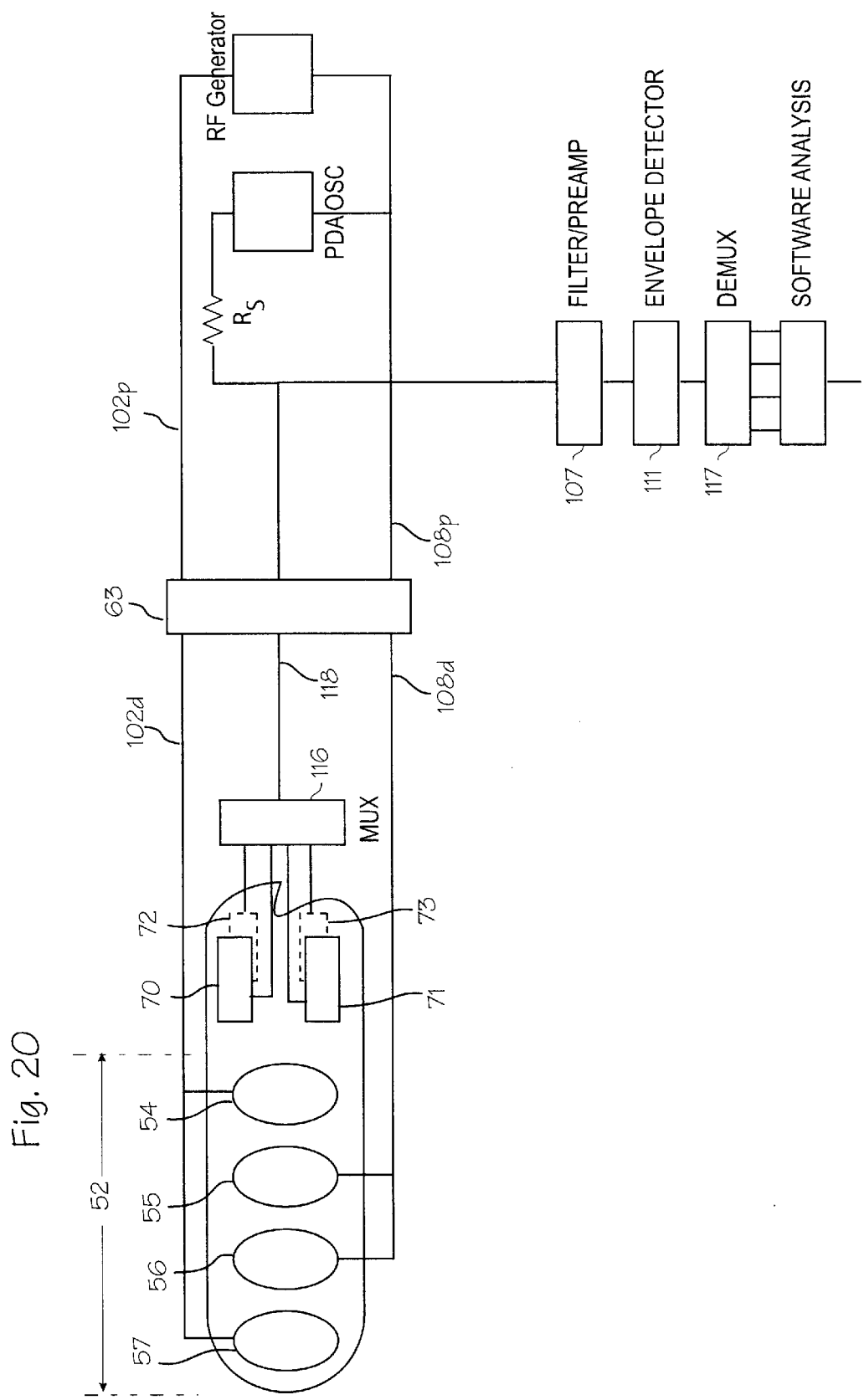
FIG. 20 illustrates the use of multiplexing circuits in the position detection circuitry.

FIG. 20 illustrates the use of multiplexing circuits in the position detection circuitry. In this circuit, the multiplexer 116 is placed in the catheter itself, close to the PDA electrodes, and the four wires 110, 112, 113 and 114 needed in FIG. 19 are replaced by a single conductor 118 communicating between the multiplexer and the filter preamp 107. Output from the filter/preamp and envelope detector are demultiplexed by demultiplexer 117. Thus, a single impedance sensing circuit polls each position detection electrode sequentially, and repeatedly, through a single conductor running through the cable and catheter.

We have described the various devices and methods in the context of placing a catheter in the fallopian tube. However, they may be used in various other lumens and vessels of the body. While we have discussed the use of RF energy for powering the circuit, AC power or pulsed DC power may be used. The position detecting system may be used with the wounding segment described herein, or other treatment systems such coil placement, chemical ablation or therapeutic delivery, laser treatment, heat treatment, or cryoablation or stent delivery systems and many other treatment systems.

The benefits of the dual or multi-threshold detection system can also be achieved with position detection arrays of various geometries, included longitudinally dispersed ring electrodes. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for treating the ovarian pathway of a female patient, through transcervical placement of a catheter into the ovarian pathway of the patient, said system comprising:
    a catheter adapted for transcervical introduction into the ovarian pathway;
    a treatment segment disposed on the distal tip of the catheter;
    an impedance detection circuit comprising an array of position detection electrodes disposed on the catheter in the proximity of the treatment segment such that the position electrodes will contact the ovarian pathway upon insertion of the catheter into the ovarian pathway, and an impedance measuring circuit operably connected to the electrodes of the array, said impedance measuring circuit being operable to provide an output corresponding to the impedance of the impedance detection circuit measured at the position detection electrodes;
    a control box comprising a computer system and a display screen, said computer system being programmed to receive input from the impedance detection circuit corresponding the impedance measured at the electrodes of the array and create a display indicating the degree of contact between the electrodes and the ovarian pathway based on the measured impedance;
    wherein the position detection electrodes are arranged circumferentially about the catheter, in circuit with a return electrode also disposed on the catheter; and
    the computer system is further programmed to create the display comprising a circular image divided into radial segments, the number radial segments corresponding to the number of position detection electrodes, and associate each radial segment with a position detection electrode, and provide visual indication within the radial segments corresponding to the impedance measured at the associated position detection electrode.

2. The system of claim 1 wherein:
    the computer system is further programmed to determine that a position detection electrode is in a first degree of contact with the ovarian pathway, and alter the display accordingly, when the impedance measured at the electrode falls into a first predetermined range and the impedance measured at all electrodes falls within a second predetermined range.

3. The system of claim 2 wherein:
    the computer system is further programmed to determine that the detection electrode is in a second degree of contact with the ovarian pathway, and alter the display accordingly to provide an additional visual indication, when the impedance measured at the electrode falls into a first predetermined range and the impedance measured at all electrodes falls within a third predetermined range.

4. The system of claim 3 wherein the first predetermined range is zero to 30 Kohm, the second predetermined range is about 17 Kohm, and the third range is about 4 Kohm.

5. The system of claim 3 wherein:

the position detection electrodes comprise four electrodes disposed circumferentially around the distal end of the catheter, proximal to the treatment segment; and the computer system is programmed to create a display comprising a circle divided into four radial segments, and is further programmed to alter the appearance of the four radial segments based on the impedance measured at the four electrodes.

6. The system of claim 2 wherein:

the position detection electrodes comprise four electrodes disposed circumferentially around the distal end of the catheter, proximal to the treatment segment; and the computer system is programmed to create a display comprising a circle divided into four radial segments, and is further programmed to alter the appearance of the four radial segments based on the impedance measured at the four electrodes.

7. The system of claim 1 wherein:

the position detection electrodes comprise four electrodes disposed circumferentially around the distal end of the catheter, proximal to the treatment segment; and the computer system is programmed to create a display comprising a circle divided into four radial segments, and is further programmed to alter the appearance of the four radial segments based on the impedance measured at the four electrodes.

8. A system for treating the ovarian pathway of a female patient, through transcervical placement of a catheter into the ovarian pathway of the patient, said system comprising:

a catheter adapted for transcervical introduction into the ovarian pathway;

a treatment seqment disposed on the distal tip of the catheter;

an impedance detection circuit comprising an array of position detection electrodes disposed on the catheter in the proximity of the treatment segment such that the position electrodes will contact the ovarian pathway upon insertion of the catheter into the ovarian pathway, and an impedance measuring circuit operably connected to the electrodes of the array, said impedance measuring circuit being operable to provide an output corresponding to the impedance of the impedance detection circuit measured at the position detection electrodes;

a control box comprising a computer system and a display screen, said computer system being programmed to receive input from the impedance detection circuit corresponding the impedance measured at the electrodes of the array and create a display indicating the degree of contact between the electrodes and the ovarian pathway based on the measured impedance;

wherein the computer system is programmed to determine that a position detection electrode is in a first degree of contact with the ovarian pathway, and alter the display accordingly, when the impedance measured at the electrode falls into a first predetermined range and the impedance measured at all electrodes falls within a second predetermined range.

9. The system of claim 8 wherein:

the computer system is programmed to determine that the detection electrode is in a second degree of contact with the ovarian pathway, and alter the display accordingly to provide an additional visual indication, when the impedance measured at the electrode falls into a first predetermined range and the impedance measured at all electrodes falls within a third predetermined range.

10. The system of claim 9 wherein the first predetermined range is zero to 30 Kohm, the second predetermined range is about 17 Kohm, and the third range is about 4 Kohm.

11. The system of claim 9 wherein:

the position detection electrodes comprise four electrodes disposed circumferentially around the distal end of the catheter, proximal to the treatment segment; and the computer system is programmed to create a display comprising a circle divided into four radial segments, and is further programmed to alter the appearance of the four radial segments based on the impedance measured at the four electrodes.

12. The system of claim 7 wherein:

the position detection electrodes comprise four electrodes disposed circumferentially around the distal end of the catheter, proximal to the treatment segment; and the computer system is programmed to create a display comprising a circle divided into four radial segments, and is further programmed to alter the appearance of the four radial segments based on the impedance measured at the four electrodes.

13. A system for treating the ovarian pathway of a female patient, through transcervical placement of a catheter into the ovarian pathway of the patient, said system comprising:

a catheter adapted for transcervical introduction into the ovarian pathway;

a treatment segment disposed on the distal tip of the catheter;

an impedance detection circuit comprising an array of position detection electrodes disposed on the catheter in the proximity of the treatment seqment such that the position electrodes will contact the ovarian pathway upon insertion of the catheter into the ovarian pathway, and an impedance measuring circuit operably connected to the electrodes of the array, said impedance measuring circuit being operable to provide an output corresponding to the impedance of the impedance detection circuit measured at the position detection electrodes;

a control box comprising a computer system and a display screen, said computer system being programmed to receive input from the impedance detection circuit corresponding the impedance measured at the electrodes of the array and create a display indicating the degree of contact between the electrodes and the ovarian pathway based on the measured impedance;

wherein the treatment segment comprises at least one wounding element and the control box includes treatment means for applying energy to the ovarian pathway through the wounding element, and input means for receiving input from an operator to initiate application of energy;

the computer system is operably connected to the treatment means, and the computer system is further programmed to determine, based on the measured impedance, when the catheter has achieved a predetermined degree of contact with the ovarian pathway, and control operability of the treatment means based on the degree of contact; and the computer system is further programmed to alter the display to inform an operator when the computer system has determined that the predetermined degree of contact has been lost, provide a visual indication of loss of contact, and interrupt application of energy when the predetermined degree of contact has been lost.

14. A system for treating the ovarian pathway of a female patient, through transcervical placement of a catheter into the ovarian pathway of the patient, said system comprising:
- a catheter adapted for transcervical introduction into the ovarian pathway;
- a treatment seqment disposed on the distal tip of the catheter;
- an impedance detection circuit comprising an array of position detection electrodes disposed on the catheter in the proximity of the treatment segment such that the position electrodes will contact the ovarian pathway upon insertion of the catheter into the ovarian pathway, and an impedance measuring circuit operably connected to the electrodes of the array, said impedance measuring circuit being operable to provide an output corresponding to the impedance of the impedance detection circuit measured at the position detection electrodes;
- a control box comprising a computer system and a display screen, said computer system being programmed to receive input from the impedance detection circuit corresponding the impedance measured at the electrodes of the array and create a display indicating the degree of contact between the electrodes and the ovarian pathway based on the measured impedance;
- wherein the treatment segment comprises at least one wounding element, and the control box includes treatment means for applying energy to the ovarian pathway through the wounding element, and input means for receiving input from an operator to initiate application of energy;
- the computer system is operably connected to the treatment means, and the computer system is further programmed to determine, based on the measured impedance, when the catheter has achieved a predetermined degree of contact with the ovarian pathway, and control operability of the treatment means based on the degree of contact; and
- the computer system is further programmed operate the treatment means for a predetermined treatment period upon receipt of operator input to initiate application of energy.

15. The system of claim 14, wherein:
the computer system is further programmed to alter the display to inform an operator when the computer system has determined that the predetermined degree of contact has been lost, provide a visual indication of loss of contact, and interrupt application of energy when the predetermined degree of contact has been lost.

16. The system of claim 15, wherein:
the computer system is further programmed, upon determining loss of contact between the catheter and ovarian pathway, to prompt the operator to reposition the catheter and reinitiate application energy for an entire predetermined treatment period.

17. A system for treating the ovarian pathway of a female patient, through transcervical placement of a catheter into the ovarian pathway of the patient, said system comprising:
- a catheter adapted for transcervical introduction into the ovarian pathway;
- a treatment seqment disposed on the distal tip of the catheter;
- an impedance detection circuit comprising an array of position detection electrodes disposed on the catheter in the proximity of the treatment segment such that the position electrodes will contact the ovarian pathway upon insertion of the catheter into the ovarian pathway, and an impedance measuring circuit operably connected to the electrodes of the array, said impedance measuring circuit being operable to provide an output corresponding to the impedance of the impedance detection circuit measured at the position detection electrodes;
- a control box comprising a computer system and a display screen, computer system being programmed to receive input from the impedance detection circuit corresponding the impedance measured at the electrodes of the array and create a display indicating the degree of contact between the electrodes and the ovarian pathway based on the measured impedance;
- wherein the impedance measuring circuit further comprises:
  - an oscillator operable to provide an RF or AC impedance detection signal to the position detection electrodes; and
  - a voltage divider and envelope detector circuit for creating an output impedance signal corresponding to the impedance measured at the position detection electrodes and supplying the impedance signal to the computer system.

18. A system for treating the ovarian pathway of a female patient, through transcervical placement of a catheter into the ovarian pathway of the patient, said system comprising:
- a catheter adapted for transcervical introduction into the ovarian pathway;
- a treatment segment disposed on the distal tip of the catheter;
- an impedance detection circuit comprising an array of position detection electrodes disposed on the catheter in the proximity of the treatment segment such that the position electrodes will contact the ovarian pathway upon insertion of the catheter into the ovarian pathway, and an impedance measuring circuit operably connected to the electrodes of the array, said impedance measuring circuit being operable to provide an output corresponding to the impedance of the impedance detection circuit measured at the position detection electrodes;
- a control box comprising a computer system and a display screen, said computer system being programmed to receive input from the impedance detection circuit corresponding the impedance measured at the electrodes of the array and create a display indicating the degree of contact between the electrodes and the ovarian pathway based on the measured impedance;
- wherein the impedance measuring circuit further comprises:
  - a constant current supply operable to supply a constant current to the position detection electrodes; and
  - an envelope detector circuit for creating an output impedance signal corresponding to the voltage measured at the position detection electrodes and supplying the impedance signal to the computer system.

19. A system for treating the ovarian pathway of a female patient, through transcervical placement of a catheter into the ovarian pathway of the patient, said system comprising:
- a catheter adapted for transcervical introduction into the ovarian pathway, a treatment segment disposed on the distal tip of the catheter;
- an impedance detection circuit comprising a plurality of position detection electrodes disposed on the catheter in the proximity of the treatment segment, and arranged circumferentially about the catheter, such that the position electrodes will contact the ovarian pathway upon insertion of the catheter into the ovarian pathway, and impedance measuring circuit operably connected to the electrodes of the array, said impedance measuring circuit being operable to provide an output corresponding to the impedance of the impedance detection circuit measured at the position detection electrodes;

a control system and an indicator, said control system being designed to receive input from the impedance detection circuit corresponding to the impedance measured at the electrodes of the array and create an indication of the degree of contact between the electrodes and the ovarian pathway based on the measured impedance;

wherein the plurality of position detection electrodes are disposed on the catheter at a position proximal to the treatment segment, and the distance between the position detection electrodes and the treatment segment is chosen such that contact between the position detection electrodes and the ovarian pathway indicates that the treatment segment is positioned in a desired portion of the ovarian pathway;

wherein the treatment segment is about 1 to 2 mm in diameter and the distance between the position detection electrodes and the treatment segment is about 1.5 mm.

20. A system for treating the ovarian pathway of a female patient, through transcervical placement of a catheter into the ovarian pathway of the patient, said system cormprising:

a catheter adapted for transcervical introduction into the ovarian pathway, a treatment segment disposed on the distal tip of the catheter;

an impedance detection circuit comprising a plurality of position detection electrodes disposed on the catheter in the proximity of the treatment segment, and arranged circumferentially about the catheter, such that the position electrodes will contact the ovarian pathway upon insertion of the catheter into the ovarian pathway, and impedance measuring circuit operably connected to the electrodes of the array, said impedance measuring circuit being operable to provide an output corresponding to the impedance of the impedance detection circuit measured at the position detection electrodes;

a control box comprising a computer system and a display screen, said computer system being programmed to receive input from the impedance detection circuit corresponding the impedance measured at the electrodes of the array and create a display indicating the degree of contact between the electrodes and the ovarian pathway based on the measured impedance;

wherein the plurality of position detection electrodes are disposed on the catheter at a position proximal to the treatment segment, and the distance between the position detection electrodes and the treatment segment is chosen such that contact between the position detection electrodes and the ovarian pathway indicates that the treatment segment is positioned in a desired portion of the ovarian pathway;

wherein the treatment segment is about 1 to 2 mm in diameter and the distance between the position detection electrodes and the treatment segment is about 1.5 mm.

21. A system for treating the ovarian pathway of a female patient, through transcervical placement of a catheter into the ovarian pathway of the patient, said system comprising:

a catheter adapted for transcervical introduction into the ovarian pathway;

a treatment segment disposed on the distal tip of the catheter;

an impedance detection circuit comprising an array of position detection electrodes disposed on the catheter in the proximity of the treatment segment such that the position electrodes will contact the ovarian pathway upon insertion of the catheter into the ovarian pathway, and an impedance measuring circuit operably connected to the electrodes of the array, said impedance measuring circuit being operable to provide an output corresponding to the impedance of the impedance detection circuit measured at the position detection electrodes;

a control box comprising a computer system and a display screen, said computer system being programmed to receive input from the impedance detection circuit corresponding the impedance measured at the electrodes of the array and create a display indicating the degree of contact between the electrodes and the ovarian pathway based on the measured impedance;

wherein the position detection electrodes are arranged circumferentially about the catheter, in circuit with a return electrode also disposed on the catheter; and the computer system is further programmed to create the display comprising an image divided into radial segments, the number radial segments corresponding to the number of position detection electrodes, and associate each radial segment with a position detection electrode, and provide visual indication within the radial segments corresponding to the impedance measured at the associated position detection electrode.

22. The system of claim 21 wherein:

the computer system is further programmed to determine that a position detection electrode is in a first degree of contact with the ovarian pathway, and alter the display accordingly, when the impedance measured at the electrode falls into a first predetermined range and the impedance measured at all electrodes falls within a second predetermined range.

23. The system of claim 22 wherein:

the computer system is further programmed to determine that the detection electrode is in a second degree of contact with the ovarian pathway, and alter the display accordingly to provide an additional visual indication, when the impedance measured at the electrode falls into a first predetermined range and the impedance measured at all electrodes falls within a third predetermined range.

24. The system of claim 23 wherein the first predetermined range is zero to 30 Kohm, the second predetermined range is about 17 Kohm, and the third range is about 4 Kohm.

25. The system of claim 23 wherein:

the position detection electrodes comprise four electrodes disposed circumferentially around the distal end of the catheter, proximal to the treatment segment; and the computer system is programmed to create a display comprising a circle divided into four radial segments, and is further programmed to alter the appearance of the four radial segments based on the impedance measured at the four electrodes.

26. The system of claim 22 wherein:

the position detection electrodes comprise four electrodes disposed circuinferentially around the distal end of the catheter, proximal to the treatment segment; and the computer system is programmed to create a display comprising a circle divided into four radial segments, and is further programmed to alter the appearance of the four radial segments based on the impedance measured at the four electrodes.

27. The system of claim 21 wherein:

the position detection electrodes comprise four electrodes disposed circumferentially around the distal end of the catheter, proximal to the treatment segment; and the computer system is programmed to create a display comprising a circle divided into four radial segments, and is further programmed to alter the appearance of the four radial segments based on the impedance measured at the four electrodes.

28. A system for treating the ovarian pathway of a female patient, through transcervical placement of a catheter into the ovarian pathway of the patient, said system comprising:

a catheter adapted for transcervical introduction into the ovarian pathway;

a treatment segment disposed on the distal tip of the catheter;

an impedance detection circuit comprising an array of position detection electrodes disposed on the catheter in the proximity of the treatment segment such that the position electrodes will contact the ovarian pathway upon insertion of the catheter into the ovarian pathway, and an impedance measuring circuit operably connected to the electrodes of the array, said impedance measuring circuit being operable to provide an output corresponding to the impedance of the impedance detection circuit measured at the position detection electrodes;

a control box comprising a computer system and a display screen, said computer system being programmed to receive input from the impedance detection circuit corresponding the impedance measured at the electrodes of the array and create a display indicating the degree of contact between the electrodes and the ovarian pathway based on the measured impedance;

wherein the computer system is programmed to determine that a position detection electrode is in a first degree of contact with the ovarian pathway, and alter the display accordingly, when the impedance measured at the electrode is between zero and 30 Kohm and the impedance values of all electrodes in the array are within 17 Kohm of each other.

29. The system of claim 28 wherein:

the computer system is programmed to determine that the detection electrode is in a second degree of contact with the ovarian pathway, and alter the display accordingly to provide an additional visual indication, when the impedance measured at the electrode is between zero and 30 Kohm and the impedance values of all electrodes in the array are within 4 Kohm of each other.

30. A system for treating the ovarian pathway of a female patient, through transcervical placement of a catheter into the ovarian pathway of the patient, said system comprising:

a catheter adapted for transcervical introduction into the ovarian pathway;

a treatment segment disposed on the distal tip of the catheter;

an impedance detection circuit comprising an array of position detection electrodes disposed on the catheter in the proximity of the treatment segment such that the position electrodes will contact the ovarian pathway upon insertion of the catheter into the ovarian pathway, and an impedance measuring circuit operably connected to the electrodes of the array, said impedance measuring circuit being operable to provide an output corresponding to the impedance of the impedance detection circuit measured at the position detection electrodes;

a control box comprising a computer system and a display screen, said computer system being programmed to receive input from the impedance detection circuit corresponding the impedance measured at the electrodes of the array and create a display indicating the degree of contact between the electrodes and the ovarian pathway based on the measured impedance;

wherein the position detection electrodes are arranged circumferentially about the catheter, in circuit with a return electrode also disposed on the catheter;

the computer system is further programmed to create the display comprising an image divided into radial segments, the number radial segments corresponding to the number of position detection electrodes, and associate each radial segment with a position detection electrode, and provide visual indication within the radial segments corresponding to the impedance measured at the associated position detection electrode; and the computer system is further programmed to determine that a position detection electrode is in a first degree of contact with the ovarian pathway, and alter the display accordingly, when the impedance measured at the electrode is between zero and 30 Kohm and the impedance values of all electrodes in the array are within 17 Kohm of each other.

31. The system of claim 30 wherein:

the computer system is further programmed to determine that the detection electrode is in a second degree of contact with the ovarian pathway, and alter the display accordingly to provide an additional visual indication, when the impedance measured at the electrode is between zero and 30 Kohm and the impedance values of all electrodes in the array are within 4 Kohm of each other.

* * * * *